United States Patent [19]

Szerenyi et al.

[11] Patent Number: 4,517,135
[45] Date of Patent: May 14, 1985

[54] CARBONATION MEASURING SYSTEM AND PROCESS

[75] Inventors: Peter Szerenyi, Cross River; Colin J. Ringleib, Shenorock, both of N.Y.

[73] Assignee: PepsiCo, Inc., Purchase, N.Y.

[21] Appl. No.: 506,701

[22] Filed: Jun. 21, 1983

[51] Int. Cl.³ .............................................. B01F 3/04
[52] U.S. Cl. .................................. 261/104; 73/61 R; 250/336.1; 261/DIG. 7; 374/44; 422/68
[58] Field of Search ......................... 261/104, DIG. 7; 73/61 R; 250/336.1; 422/68; 374/44; 426/477; 99/323.1

[56] References Cited

U.S. PATENT DOCUMENTS

| | | | |
|---|---|---|---|
| 2,939,311 | 6/1960 | Booth | 261/104 X |
| 3,007,333 | 11/1961 | Chadenson | 374/44 X |
| 3,532,270 | 10/1970 | Schoen, Jr. | 261/104 X |
| 3,572,994 | 3/1971 | Hochstrasser | 261/104 X |
| 3,618,911 | 11/1971 | Martin | 261/104 |
| 3,780,198 | 12/1973 | Pahl et al. | 261/DIG. 7 |
| 3,788,545 | 1/1974 | Budd et al. | 261/104 X |
| 3,824,836 | 7/1974 | Lyshkow | 261/104 X |
| 3,833,016 | 9/1974 | Lucero et al. | 261/104 X |
| 3,904,849 | 9/1975 | Lucero et al. | 261/104 X |
| 4,063,094 | 12/1977 | Schuman | 250/336.1 X |

*Primary Examiner*—Richard L. Chiesa
*Attorney, Agent, or Firm*—Scully, Scott, Murphy & Presser

[57] ABSTRACT

An arrangement for measuring the carbonation level of a liquid, useful for controlling the extent of carbonation of a beverage, particularly in a continuous process stream. A portion of the process stream is diverted to flow adjacent to a gas permeable membrane having a diluent gas such as helium or nitrogen flowing on the opposite side thereof. The diluent gas stream absorbs carbon dioxide in proportion to the extent of carbonation of the beverage, and a suitable characteristic, such as thermal conductivity or infrared absorption, of the diluent gas and carbon dioxide mixture is then measured as an indication of the carbonation level of the beverage.

17 Claims, 2 Drawing Figures

CARBONATION MEASURING SYSTEM AND PROCESS

BACKGROUND OF THE INVENTION

1. Field of the Invention

The present invention relates generally to a system and process for measuring the carbonation level of a liquid, and more particularly pertains to an arrangement of the aforementioned type having utility in the production of carbonated beverages, particularly in a continuous process stream operation producing substantial quantities of carbonated beverages, such as in a beverage bottling plant. Alternatively, the subject invention might be used to monitor the carbonation level of discrete bottles of carbonated beverages. Additionally, the present invention might also have utility in connection with the purveying or dispensing of carbonated beverages for immediate consumption at the point of sale, for example at a soda fountain.

The subject invention is useful in connection with both soft beverage operations and hard or alcoholic beverage (e.g. malted beverages such as beer, ale, and malt liquors) operations. The present invention also has direct utility in the measurement of carbonation levels of liquids other than beverages.

2. Discussion of the Prior Art

Water has a rather marked affinity for carbon dioxide, and will absorb substantial quantities thereof when that gas is brought into contact with the water's surface. The degree of absorption depends upon several factors, including the temperature of the water and the gas and also upon the pressure under which the gas contacts the water surface. As is well known to those familiar with the carbonation arts, an increase in pressure will result in an increase in the amount of carbon dioxide absorbed by a given quantity of water at a particular temperature. Furthermore, a decrease in the temperature of the water will result in increased absorption at a given pressure. The rate of speed with which water will absorb carbon dioxide at a given temperature and pressure is also determined by the amount of surface areas of the water brought into contact with the gas. There are a number of variables which can effect the level of carbonation of a liquid such as a beverage. However, the measurement of the carbonation level of a beverage has presented unique problems, particularly in an on-line continuous process stream operation. Such beverage carbonation operations would benefit directly from an accurate measurement of the amount of carbon dioxide already absorbed by the water, which would assist in the production of a high quality, substantially uniformly carbonated beverage.

SUMMARY OF THE INVENTION

Accordingly, it is a primary object of the present invention to provide a system and process for providing an accurate measurement of the amount of carbon dioxide already absorbed by a liquid.

A further object of the subject invention is the provision of a process and system of the aforementioned type having general utility in carbonated beverage operations, particularly in a continuous process stream operation such as in a beverage bottling plant.

In accordance with the teachings herein, the present invention provides a process and system for measuring the carbonation level of a liquid in which the liquid is contacted with a first side of a gas permeable element, such that carbon dioxide permeates therethrough substantially in proportion in the extent of carbonation of the liquid. A diluent gas is contacted with a second, opposite side of the gas permeable element, such that carbon dioxide permeating therethrough is picked up by the diluent gas. The concentration of carbon dioxide in the diluent gas is then detected to provide a measurement of the extent of carbonation of the liquid.

The present invention is directly useful to control the pressure of carbon dioxide applied to water in a beverage carbonation operation, and is particularly useful in a continuous process beverage carbonation operation wherein the carbonated water flows continuously by the first side of the gas permeable element, and the diluent gas flows continuously by the second side thereof.

The arrangement includes an enclosure separated by the gas permeable element into a first chamber, through which the carbonated water flows in a continuous manner, and a second chamber through which the diluent gas flows continuously. In the preferred embodiment, the enclosure includes a thermostatic control system associated therewith such that the temperature of both the water and the diluent gas is regulated to a controlled temperature prior to their contacting the gas permeable element. In separate disclosed embodiments, either the thermal conductivity or the radiation absorption characteristics of the diluent gas/carbon dioxide mixture is measured to provide a measurement of the carbonation level in the water.

BRIEF DESCRIPTION OF THE DRAWINGS

The foregoing object and advantages of the present invention for a carbonation measuring system and process may be more readily understood by one skilled in the art with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

Figure 1:
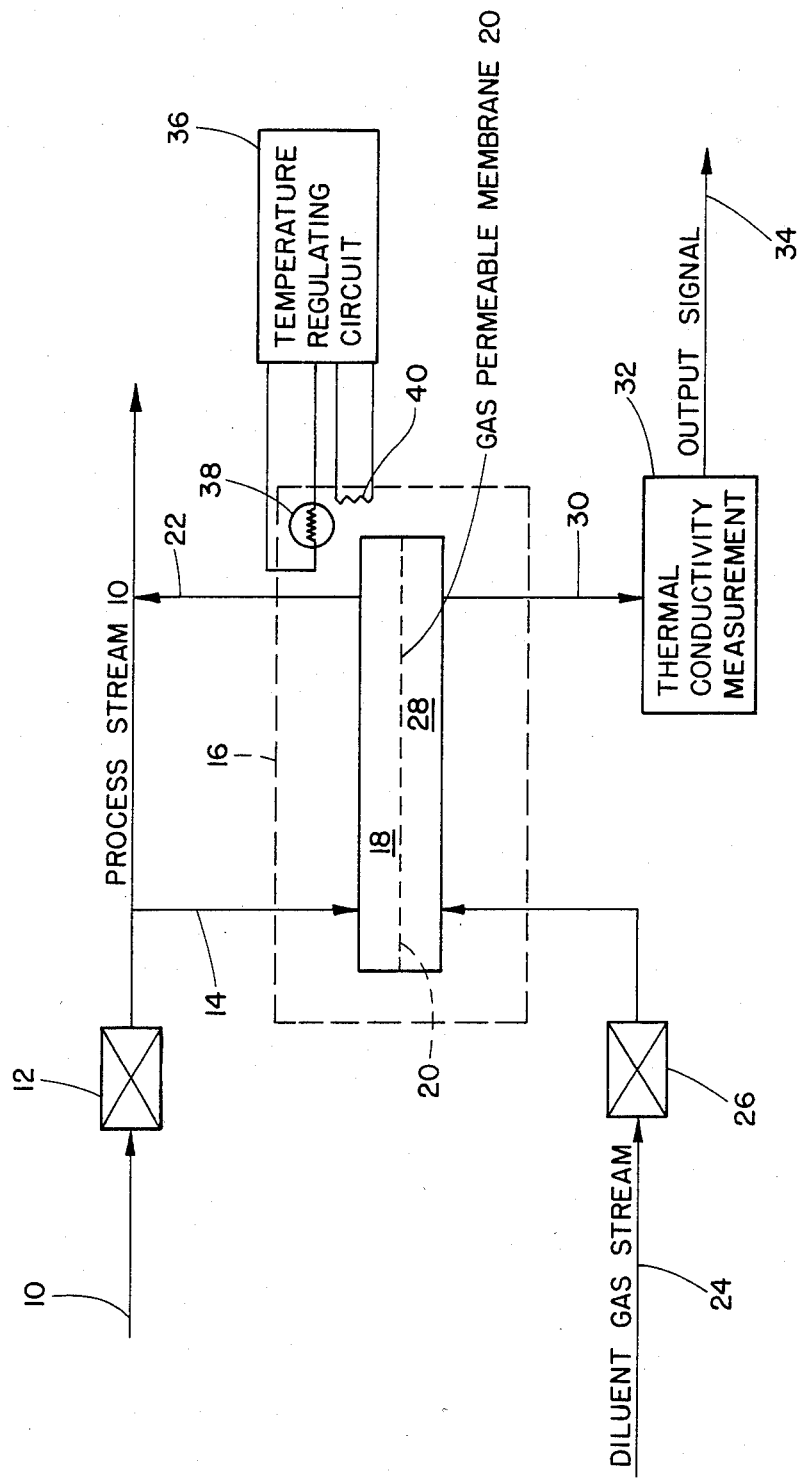
FIG. 1 is a schematic flow diagram of a first exemplary embodiment of a carbonation measuring system and process constructed pursuant to the teachings of the present invention.

Referring to the drawings in detail, FIG. 1 illustrates a first embodiment of the present invention wherein a process stream 10 of carbonated water from a continuous process stream carbonation operation is directed through a flow controller valve 12, which controls the rate of flow therethrough. A portion of the process stream 10 is diverted to a measurement stream 14 into a housing or enclosure 16 wherein the beverage is directed into a first chamber 18 in which it contacts a first side of a gas permeable element in the form of a membrane 20. The carbonated beverage is pumped through the system under a pressure which is above the vapor pressure of carbon dioxide, typically below 100 psi. The beverage eventually flows from the first chamber 18 in a stream 22 which rejoins the main process stream 10. During operation of the illustrated measuring system, carbon dioxide will permeate from the carbonated beverage through the membrane 20 generally in proportion to the concentration of carbon dioxide absorbed in the beverage.

A diluent gas stream 24 is directed through a flow controller valve 26, which controls the rate of flow therethrough, to the enclosure 16 wherein the diluent gas is directed into a second chamber 28 in which it contacts the second, opposite side of the gas permeable membrane 20. The diluent gas can be any suitable gas for the purposes of the present invention, such as helium, nitrogen, etc. The diluent gas mixes in the second chamber with the carbon dioxide passing through the permeable membrane 20, and the diluent gas and carbon dioxide mixture then flows from the second chamber in a stream 30 to a measuring instrument 32 which examines the gas mixture and produces an electrical output signal on line 34 which is indicative of the concentration of carbon dioxide in the carbon dioxide, diluent gas mixture, and therefore is also indicative of the concentration of carbon dioxide in the beverage. The flow valves 12 and 26 are provided to obtain precisely controlled rates of flow for both the beverage and the diluent gas to ensure that the concentration measurement of carbon dioxide is not adversely affected by varying flow rates.

The output signal 34 is in the form of a continuous readout signal, and can be displayed to operating personnel or recorded, with the signal processing being in either an analog or a digital mode. The output signal can also be utilized as a process control signal, as explained in greater detail with reference to FIG. 2.

The housing or enclosure 16 with the gas permeable membrane 20 dividing it into first and second chambers 18 and 28 is a very important feature of the present invention. The gas permeable membrane can be constructed of any suitable material, and should be sufficiently strong to withstand the stress caused by a possible pressure differential between the chambers. Moreover, the enclosure should be designed to be easily cleanable and sanitizable since it directly contacts a comestible product, and the gas permeable membrane should be easily accessible and removably mounted such that it can be conveniently replaced at suitable intervals.

The measuring instrument 32 can monitor any one of several properties of the gas mixture to measure the concentration of carbon dioxide therein. The measuring instrument in the embodiment of FIG. 1 measures the thermal conductivity of the gas mixture, which is generally defined as the time rate of transfer of heat by conduction, through unit thickness, across unit area, for unit difference of temperature. At 0° C., the thermal conductivity of carbon dioxide is given as $\lambda = 3.393 \times 10^{-5}$, while that of helium is given at $\lambda = 33.60 \times 10^{-5}$, and that of nitrogen is given at $\lambda = 5.68 \times 10^{-5}$, where $\lambda$ is defined in g. —cal./(sec.) (sq.cm.) (°C./cm.) (Lange's Handbook of Chemistry, Ninth Edition, 1956). Accordingly, the presence of carbon dioxide in the gas mixture will tend to lower the thermal conductivity of the mixture in proportion to the concentration of carbon dioxide therein. Helium would appear to be a more suitable diluent gas for this embodiment as its thermal conductivity is more greatly different from that of carbon dioxide than the thermal conductivity of nitrogen. Thermal conductivity is also a temperature dependent function, and at 100° C., the thermal conductivity of carbon dioxide is given at $\lambda = 5.06 \times 10^{-5}$, while that of helium is given at $\lambda = 39.85 \times 10^{-5}$, and that of nitrogen is given at $\lambda = 7.18 \times 10^{-5}$.

The enclosure 16 is preferably temperature regulated to ensure uniformity of permeation of the carbon dioxide through the membrane 20 and also uniformity of the measurement. The temperature regulation system 36 is illustrated schematically, and includes a temperature sensor 38, which can be a thermistor or any other suitable device, and an ohmic heating element 40, both of which are positioned appropriately within the enclosure 16.

Figure 2:
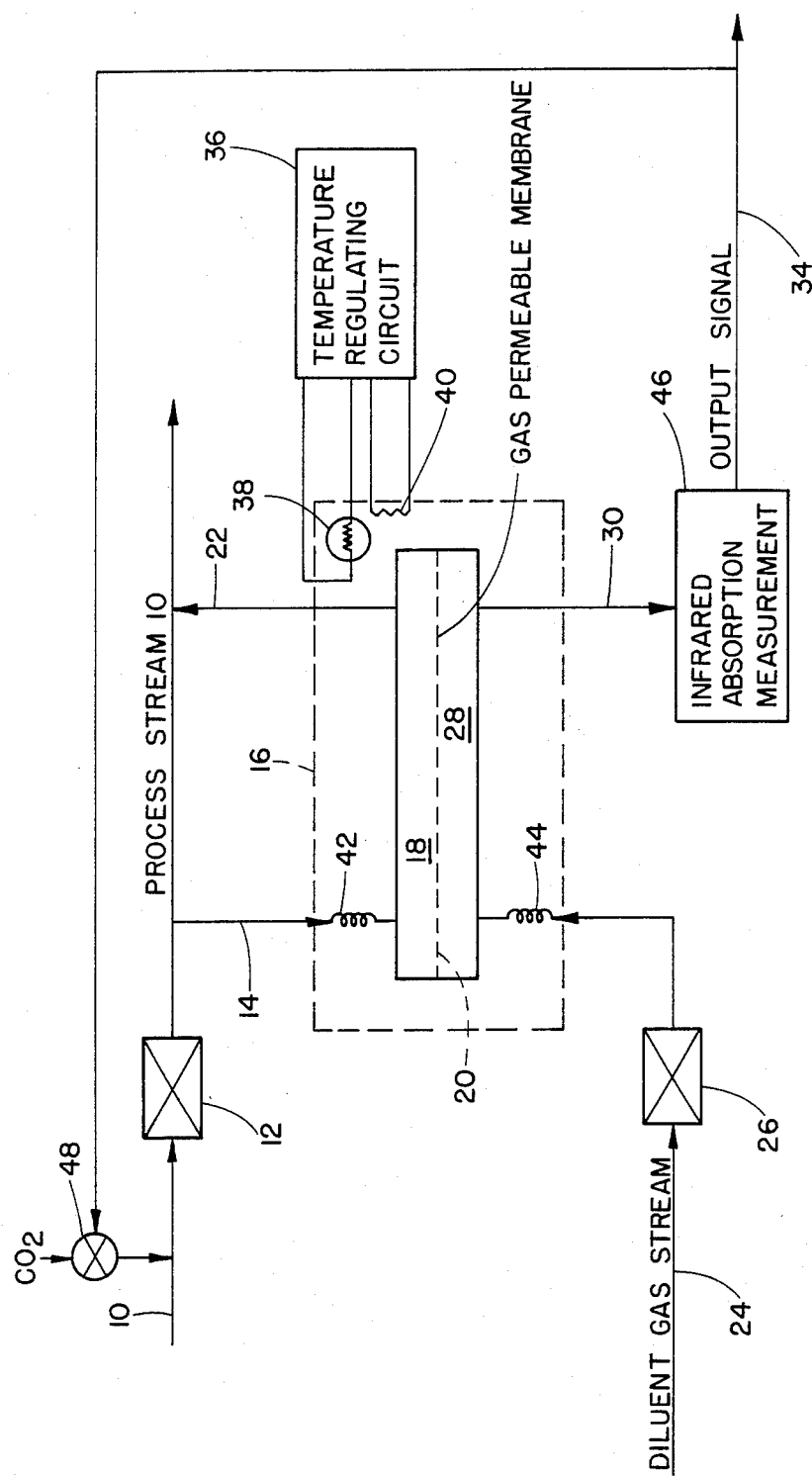
FIG. 2 illustrates a schematic flow diagram of a second exemplary embodiment of the subject invention.

FIG. 2 illustrates a second embodiment of the present invention similar in several respects to the embodiment just explained. As illustrated, the carbonated beverage in stream 14 can be directed through a lengthy flow path 42, shown as a coil, in the enclosure 16 to assist the beverage in becoming thermally stabilized at the temperature of the enclosure 16 before being directed into the first chamber 18. Likewise, the diluent gas can be directed through a lengthy flow path 44, also shown as a coil, in the enclosure 16 to assist the diluent gas in becoming thermally stabilized at the temperature of the enclosure 16 prior to being directed into the second chamber 28. In many situations when the beverage and the diluent gas enter the housing, all will be at different temperatures. The flow paths 42 and 44 effectively provide heat exchangers between both the beverage and the diluent gas and the housing to provide a thermally stabilized measurement, such that thermal variables do not adversely affect the carbon dioxide concentration measurement.

The measuring instrument 46 of FIG. 2 measures the radiation absorption characteristics of the gas mixture as a measure of the concentration of carbon dioxide therein. In greater particularity, the radiation absorption characteristics of one portion of the spectrum, such as the infrared absorption characteristics, for example at 2349 cm $-1$ can be measured and calibrated.

As illustrated schematically in FIG. 2, the output signal 34 can be directed as a feedback control signal to a pressure control valve 48 to control the pressure of the carbon dioxide gas applied to the beverage during the carbonation process.

While several embodiments and variations of the present invention for a carbonation measuring system and process are described in detail herein, it should be apparent that the disclosure and teachings of the present invention will suggest many alternative designs to those skilled in the art.

What is claimed is:
1. A process for continuously measuring the carbonation level of a carbonated and pressurized water based liquid beverage having carbon dioxide under pressure applied thereto, in a beverage carbonation process, from a continuous process stream, comprising the steps of:
  a. continuously contacting a first side of a gas permeable element with the carbonated and pressurized liquid beverage from the continuous process stream such that carbon dioxide permeates through the element substantially in proportion to the extent of carbonation of the liquid beverage;
  b. continuously contacting a second opposite side of said gas permeable element with a diluent gas stream such that carbon dioxide permeating through the element is picked up by the diluent gas stream;

c. continuously detecting the concentration of carbon dioxide in the diluent gas stream to provide a continuous measurement of the extent of carbonation of the liquid beverage in the continuous process stream; and d. utilizing the result of said detecting step to control the carbonation of the beverage in the carbonation process to obtain a carbonated beverage having a suitable beverage carbonation level.

2. A process for measuring the carbonation level of a liquid as claimed in claim 1, in a beverage carbonation process wherein the carbon dioxide under pressure is applied to the beverage and said step of utilization includes controlling the pressure of carbon dioxide applied to the water during the carbonation process to obtain a carbonated beverage having a suitable beverage carbonation level.

3. A process for measuring the carbonation level of a liquid as claimed in claim 1, further comprising the steps of utilizing a gas permeable membrane as said gas permeable element, and providing an enclosure for the gas permeable membrane defining a first chamber for the liquid on the first side of the gas permeable membrane and a second chamber for the diluent gas on the second side of the gas permeable membrane.

4. A process for measuring the carbonation level of a liquid as claimed in claim 3, further comprising the step of controlling the temperature of both the liquid and the diluent gas in said enclosure.

5. A process for measuring the carbonation level of a liquid as claimed in claim 4, said step of detecting including the step of measuring the thermal conductivity of the diluent gas stream and carbon dioxide mixture.

6. A process for measuring the carbonation level of a liquid as claimed in claim 4, said step of detecting including the step of measuring the radiation absorption characteristics of the diluent gas stream and carbon dioxide mixture.

7. A process for measuring the carbonation level of a liquid as claimed in claim 1, said step of continuously contacting a first side of a gas permeable element with the carbonated and pressurized liquid comprising contacting said first side of the gas permeable element with only the carbonated and pressurized liquid, without additional additives therein.

8. A process for measuring the carbonation level of a liquid as claimed in claim 1, including the steps of removing the carbonated and pressurized liquid from the continuous process stream for passage by said first side of the gas permeable element, and then returning the carbonated and pressurized liquid back to said continuous process stream after passage by said first side of the gas permeable element.

9. A system for continuously measuring the carbonation level of a carbonated and pressurized water based liquid beverage, having carbon dioxide applied thereto, in a beverage carbonation system, from a continuous process stream comprising:

a. an enclosure separated by a gas permeable element into first and second chambers;

b. means for continuously introducing the carbonated and pressurized liquid beverage from the continuous process stream into said first chamber adjacent to a first side of said gas permeable element;

c. means for continuously introducing a diluent gas stream into said second chamber adjacent to a second, opposite side of said gas permeable element, such that carbon dioxide permeating through the element is picked up by the diluent gas stream;

d. means for continuously detecting the concentration of carbon dioxide in the diluent gas stream to provide a continuous measurement of the extent of carbonation of the liquid beverage from the continuous process stream;

e. means, coupled to said detecting means, for controlling the carbonation of the beverage in the beverage carbonation system to obtain a carbonated beverage having a suitable beverage carbonation level.

10. A system for measuring the carbonation level of a liquid as claimed in claim 9, in a beverage carbonation system wherein said means for controlling the carbonation of the beverage further comprises means for controlling the pressure level at which the carbon dioxide is applied to the water in the carbonation system to obtain a carbonated beverage having a suitable beverage carbonation level.

11. A system for measuring the carbonation level of a liquid as claimed in claim 8, said gas permeable element comprising a gas permeable membrane.

12. A system for measuring the carbonation level of a liquid as claimed in claim 11, further comprising means, associated with said enclosure, for controlling the temperature of both the liquid and the diluent gas in said enclosure.

13. A system for measuring the carbonation level of a liquid as claimed in claim 12, said detecting means including means for measuring the thermal conductivity of the diluent gas and carbon dioxide mixture.

14. A system for measuring the carbonation level of a liquid as claimed in claim 12, said detecting means including means for measuring the radiation absorption characteristics of the diluent gas and carbon dioxide mixture.

15. A system for measuring the carbonation level of a liquid as claimed in claim 14, said detecting means including means for measuring the infrared absorption characteristics of the diluent gas.

16. A system for measuring the carbonation level of a liquid as claimed in claim 9, said means for continuously introducing the carbonated and pressurized liquid to a first side of said gas permeable membrane comprising means for continuously introducing only the carbonated and pressurized liquid, without additional additives therein.

17. A system for measuring the carbonation level of a liquid as claimed in claim 9, including means for removing the carbonated and pressurized liquid from the continuous process stream for passage by said first side of the gas permeable element, and means for returning the carbonated and pressurized liquid back to said continuous process stream after passage by said first side of the gas permeable element.

* * * * *